US010560609B2
::::

(12) United States Patent  (10) Patent No.: US 10,560,609 B2
Lau  (45) Date of Patent: Feb. 11, 2020

(54) SYSTEM AND RELATED METHOD FOR SYNCHRONIZED CAPTURE OF DATA BY MULTIPLE NETWORK-CONNECTED CAPTURE DEVICES

(71) Applicant: Karl Storz Endoscopy-America, Inc., El Segundo, CA (US)

(72) Inventor: Stephen Lau, Houston, TX (US)

(73) Assignee: Karl Storz Endoscopy-America, Inc., El Segundo, CA (US)

(\*) Notice: Subject to any disclaimer, the term of this patent is extended or adjusted under 35 U.S.C. 154(b) by 186 days.

(21) Appl. No.: 15/344,116

(22) Filed: Nov. 4, 2016

(65) Prior Publication Data

US 2018/0131844 A1  May 10, 2018

(51) Int. Cl.
*H04N 5/04* (2006.01)
*H04N 5/77* (2006.01)
(Continued)

(52) U.S. Cl.
CPC ............ *H04N 5/04* (2013.01); *G06F 19/321* (2013.01); *G16H 10/60* (2018.01); *H04N 5/0733* (2013.01); *H04N 5/0736* (2013.01); *H04N 5/23206* (2013.01); *H04N 5/23245* (2013.01); *H04N 5/247* (2013.01); *H04N 5/77* (2013.01); *H04N 7/181* (2013.01); *H04N 7/188* (2013.01);
(Continued)

(58) Field of Classification Search
CPC ........ H04N 5/04; H04N 5/23245; H04N 5/77; H04N 7/181; H04N 7/188; G16H 10/60; G06F 19/321

USPC .......................................................... 348/159
See application file for complete search history.

(56) References Cited

U.S. PATENT DOCUMENTS 8,539,105 B2  9/2013 Logvinov et al.
8,599,235 B2  12/2013 Friel et al.
(Continued)

FOREIGN PATENT DOCUMENTS

EP  1883227 A2  1/2008
EP  2432370 A2  3/2012
(Continued)

OTHER PUBLICATIONS

European Search Report & Written Opinion Application No. 17199990.7 Completed: Mar. 21, 2018; dated Mar. 29, 2018 9 Pages.

*Primary Examiner* — Joseph G Ustaris
*Assistant Examiner* — Matthew David Kim
(74) *Attorney, Agent, or Firm* — Whitmyer IP Group LLC (57) ABSTRACT

A system includes at least two capture devices, each switchable from a respective idle mode to a respective recording mode upon receipt of a trigger signal from a trigger via a network. A controller saves data packets generated by the capture devices during the respective idle modes to a short-term memory, and saves data packets generated during the respective recording modes to a long-term memory such that the data packets form respective saved data streams. The synchronizer sends a sync signal to the capture devices via the network. The compensator determines respective delay periods between sending of the sync signal by the synchronizer and receipt of the sync signal by each of the capture devices, and transfers from the short-term memory to the long-term memory any data packets generated during the respective delay period.

23 Claims, 6 Drawing Sheets

(51) Int. Cl.
*H04N 7/18* (2006.01)
*H04N 5/232* (2006.01)
*H04N 21/218* (2011.01)
*H04N 21/43* (2011.01)
*H04N 5/073* (2006.01)
*H04N 21/433* (2011.01)
*H04N 21/242* (2011.01)
*H04N 21/4223* (2011.01)
*H04N 5/247* (2006.01)
*G16H 10/60* (2018.01)
*G06F 19/00* (2018.01)

(52) U.S. Cl.
CPC ..... *H04N 21/21805* (2013.01); *H04N 21/242* (2013.01); *H04N 21/4223* (2013.01); *H04N 21/4302* (2013.01); *H04N 21/4331* (2013.01); *H04N 21/4334* (2013.01)

(56) References Cited

U.S. PATENT DOCUMENTS

| | | |
|---|---|---|
| 8,692,864 B2 | 4/2014 | Angelo |
| 9,344,613 B2 | 5/2016 | Cote et al. |
| 2006/0048025 A1* | 3/2006 | Filipovic ............ G05B 23/0264 714/724 |
| 2009/0251601 A1* | 10/2009 | Ihlefeld ................ H04N 5/0733 348/521 |
| 2011/0275924 A1* | 11/2011 | McLellan .......... A61B 1/00016 600/407 |
| 2013/0321560 A1* | 12/2013 | Angelo, Sr. ............ H04N 7/152 348/14.03 |
| 2014/0237123 A1* | 8/2014 | Dave ................. H04W 52/0261 709/227 |
| 2014/0240587 A1* | 8/2014 | Cote .................... H04N 5/2256 348/371 |
| 2017/0093512 A1* | 3/2017 | Zhu ....................... H04J 3/0682 |

FOREIGN PATENT DOCUMENTS

| | | |
|---|---|---|
| JP | 2009296323 A | 12/2009 |
| WO | 2004038643 A2 | 5/2004 |
| WO | 2007005408 A2 | 1/2007 |
| WO | 2010010348 A1 | 1/2010 |
| WO | 2011121951 A1 | 10/2011 |
| WO | 2011152489 A1 | 12/2011 |

* cited by examiner

SYSTEM AND RELATED METHOD FOR SYNCHRONIZED CAPTURE OF DATA BY MULTIPLE NETWORK-CONNECTED CAPTURE DEVICES

TECHNICAL FIELD

The present disclosure generally relates to a system and related method for synchronized data capture by multiple capture devices. The present disclosure more particularly relates to a system and related method for synchronized capture of images and/or other non-image data by multiple network-connected capture devices.

BACKGROUND

It is known to provide a system with multiple digital cameras arranged to simultaneously capture a scene (e.g., a scene within a medical operating room) from multiple angles and/or multiple different scenes. A trigger can be used to aid in synchronizing the recording start and stop times of the multiple digital cameras. If the trigger is indirectly connected to the digital cameras (e.g., via one or more network connections), a trigger signal sent by the trigger might reach each of the digital cameras at a different real time, causing somewhat asynchronous recording start and stop times across the multiple digital cameras. This can be problematic if there is a need to have perfectly synchronized recordings from the multiple digital cameras, such as when there is a need to provide perfectly synchronized simultaneous playback of two or more of the recordings, and/or provide time-accurate switching between two or more of the recordings during playback.

Known techniques for synchronizing recordings from multiple digital cameras are incapable of reliably providing recordings that start and stop at the exact times that start and stop signals are sent by the trigger, especially when the digital cameras and the trigger are connected via a network. Among other things, such techniques fail to account for the fact that respective network delay times between the trigger and each of the multiple digital cameras can change relative to one another over time due to changing conditions of the network. Known techniques also lack the ability to synchronize and correlate image recordings from multiple digital cameras with other non-image data captured during image recording.

Aspects of the present invention are directed to these and other problems.

SUMMARY

According to an aspect of the present invention, a system is provided that includes a trigger, at least two capture devices, a controller, a short-term memory, a long-term memory, a synchronizer, and a compensator. The trigger is configured to generate a trigger signal. The at least two capture devices are each configured to switch from a respective idle mode to a respective recording mode upon receipt of the trigger signal via a network, and are each configured to generate data packets when operated in the respective idle mode and the respective recording mode. The data packets each include sensor data indicative of a condition sensed by a sensor of the respective capture device. The controller is configured to save data packets generated during the respective idle modes to a short-term memory, and configured to save data packets generated during the respective recording modes to a long-term memory such that the data packets form respective saved data streams. The synchronizer is configured to send a sync signal to the at least two capture devices via the network. The compensator configured to determine respective delay periods between sending of the sync signal by the synchronizer and receipt of the sync signal by each of the at least two capture devices. The compensator is further configured to transfer from the short-term memory to the long-term memory any data packets generated during the respective delay period.

According to another aspect of the present invention, a method includes the steps of: (i) connecting a trigger and a synchronizer to at least two capture devices via a network, the at least two capture devices each configured to generate data packets when operated in a respective idle mode and a respective recording mode, the data packets each including sensor data indicative of a condition sensed by a sensor of the respective capture device; (ii) sending a trigger signal generated by the trigger to the at least two capture devices via the network to thereby cause each of the at least two capture devices to switch from the respective idle mode to the respective recording mode; (iii) saving data packets generated during the respective idle modes to a short-term memory, and saving data packets generated during the recording mode to a long-term memory such that the data packets form respective saved data streams; (iv) sending a sync signal to the at least two capture devices via the network; (v) determining respective delay periods between sending of the sync signal by the synchronizer and receipt of the sync signal by each of the at least two capture devices; and (vi) transferring from the short-term memory to the long-term memory any data packets generated during the respective delay periods.

In addition to, or as an alternative to, one or more of the features described above, further aspects of the present invention can include one or more of the following features, individually or in combination:

- the trigger is configured to receive a user input and generate the trigger signal in response thereto;
- at least one of the at least two capture devices is a camera;
- the camera is at least one of a still image camera and a video image camera;
- the at least two digital cameras are each configured to generate data packets that include video image data;
- at least one of the at least two capture devices is configured to generate data packets that include non-image sensor data;
- at least one of the at least two capture devices is a medical device, and the medical device includes a sensor operable to generate sensor data indicative of a condition of a patient condition, an operating condition of the medical device, and/or an environmental condition;
- the at least two capture devices, when operated in the respective idle modes, continuously generate data packets;
- the at least two capture devices, when operated in the respective idle modes, continuously generate data packets according to a predetermined capture rate;
- the predetermined capture rate is an integer multiple or divisor of a period rate at which the sync signal is repetitively sent to the at least two capture devices;
- the data packets generated by the at least two capture devices further include metadata;
- the network is at least one the Internet, a wide-area-network, local-area-network, and a private network of computing infrastructure;

the synchronizer has a time basis that is the same as, and aligned with, respective time bases of the at least two capture devices;

the synchronizer is disposed relative to the trigger and the network such that respective delay periods between sending of the sync signal and receipt of the sync signal by each of the at least two capture devices is identical to respective delay periods between sending of the trigger signal and receipt of the trigger signal by each of the at least two capture devices;

the synchronizer is configured to repeatedly send the sync signal to the at least two capture devices via the network, and the compensator is configured to repeatedly determine the respective delay periods of the at least two capture devices;

the synchronizer is configured to repeatedly send the sync signal and the compensator is configured to repeatedly determine the respective delay periods according to a repetitive cycle;

the synchronizer includes a first synchronizer unit and a second synchronizer unit, the first synchronizer unit configured to send the sync signal to the at least two capture devices, and the second synchronizer unit configured to send the sync signal to the at least two capture devices when the first synchronization unit is unavailable to do so;

the synchronizer includes a first synchronizer unit and a second synchronizer unit, the first synchronizer unit configured to send the sync signal to a first capture device of the at least two capture devices, and the second synchronizer unit configured to send the sync signal to a second capture device of the at least two capture devices;

the first synchronizer unit and the second synchronizer unit are synchronized with one another via a connection therebetween;

the compensator is further configured to remove data packets from ends of the saved data streams to provide the saved data streams with predetermined numbers of data packets;

the compensator is further configured to transfer from the short-term memory to the long-term memory a predetermined number of data packets generated before generation of the trigger signal by the trigger; and a display configured to retrieve saved data streams from the long-term memory and replay the saved data streams for a user;

These and other aspects of the present invention will become apparent in light of the drawings and detailed description provided below.

DETAILED DESCRIPTION

Figure 1:
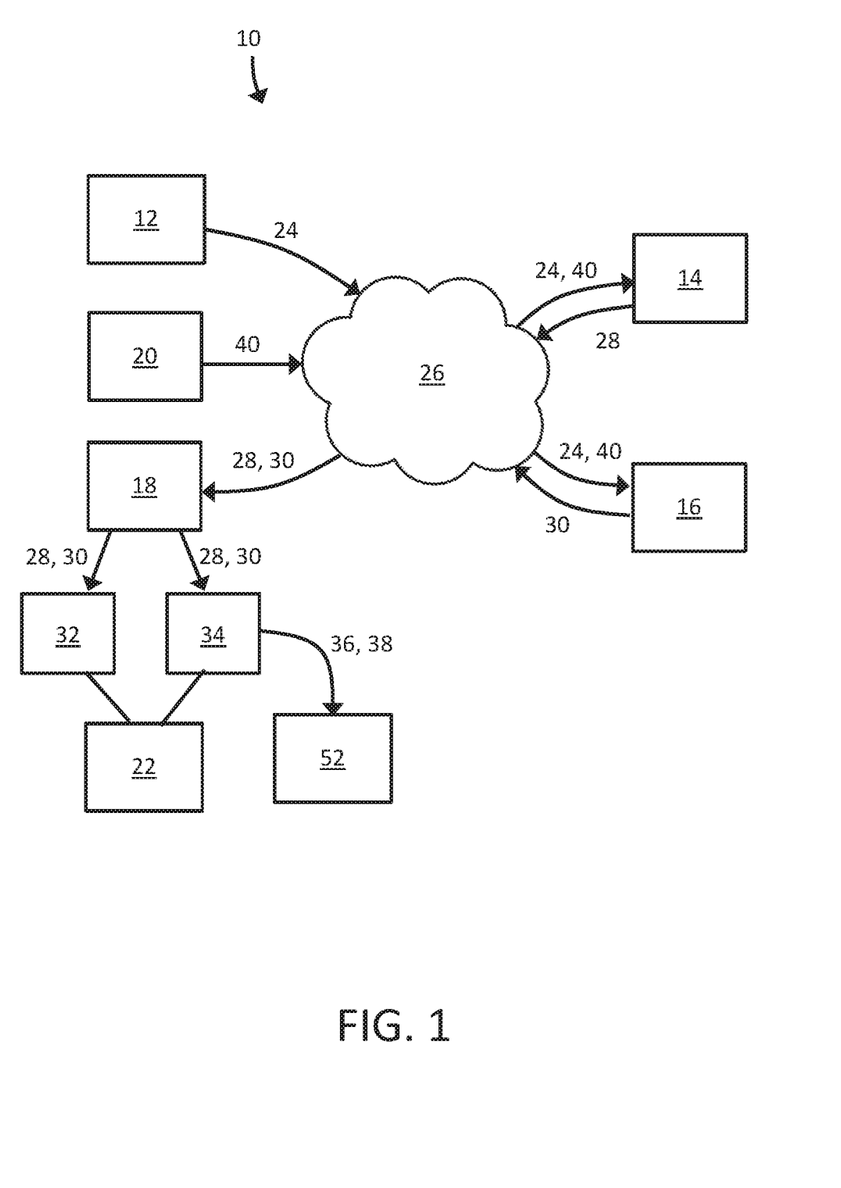
FIG. 1 schematically illustrates an embodiment of the present system.

Referring to FIG. 1, the present disclosure describes a system 10 and related method for synchronized capture of image data and other non-image data by multiple network-connected capture devices.

Figure 2:
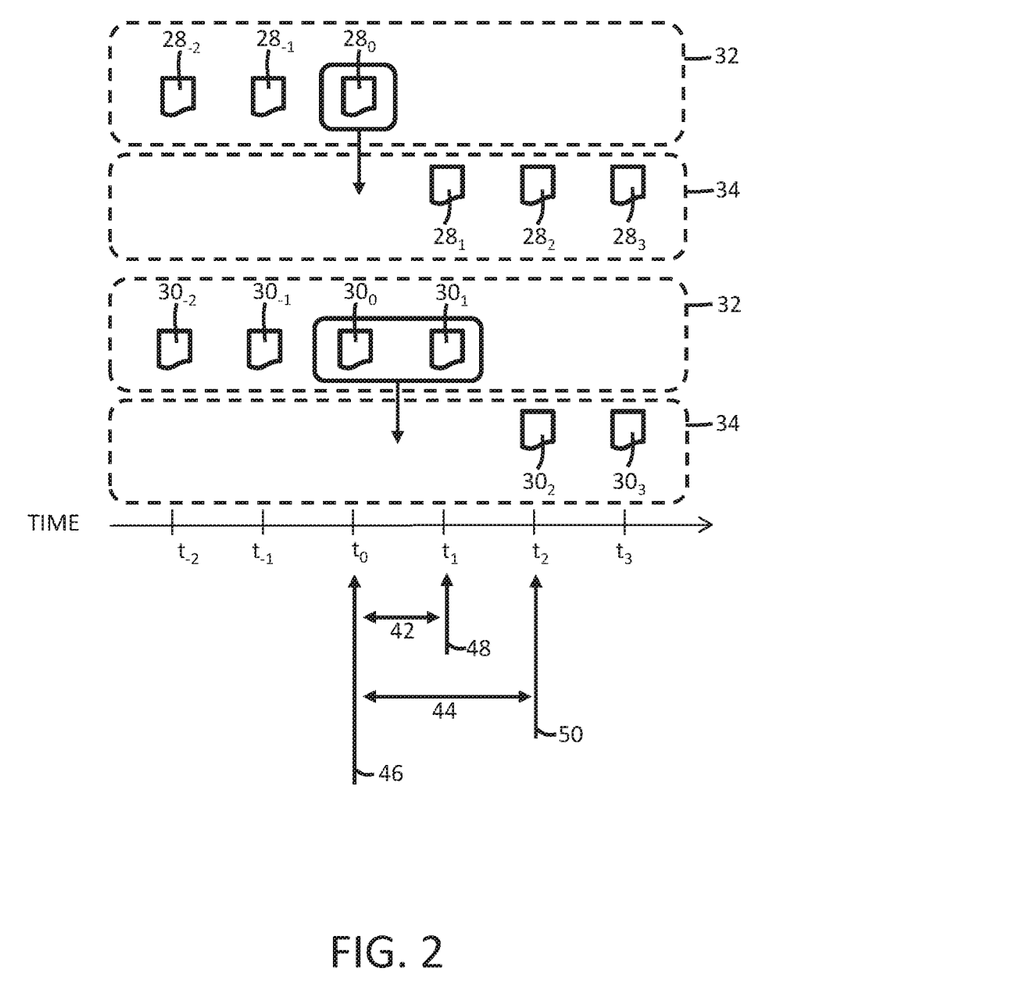
FIG. 2 schematically illustrates data packets being saved to short-term and long-term memory.
Figure 3:
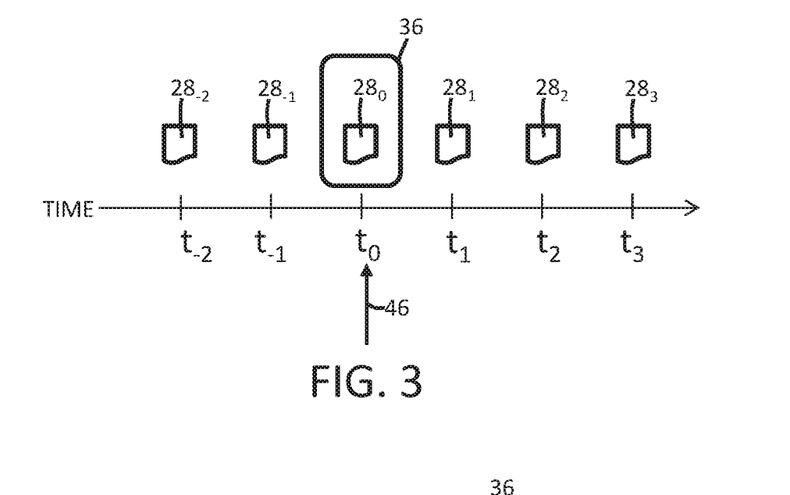
FIGS. 3-7 schematically illustrate recorded data streams generated using different recording modes.
Figure 4:
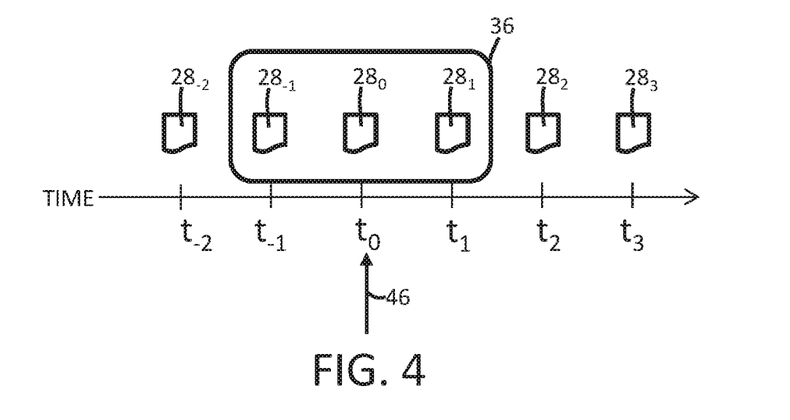
Figure 5:
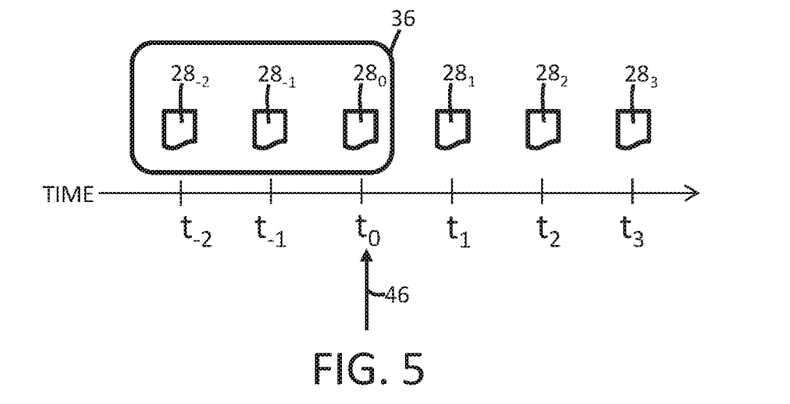
Figure 6:
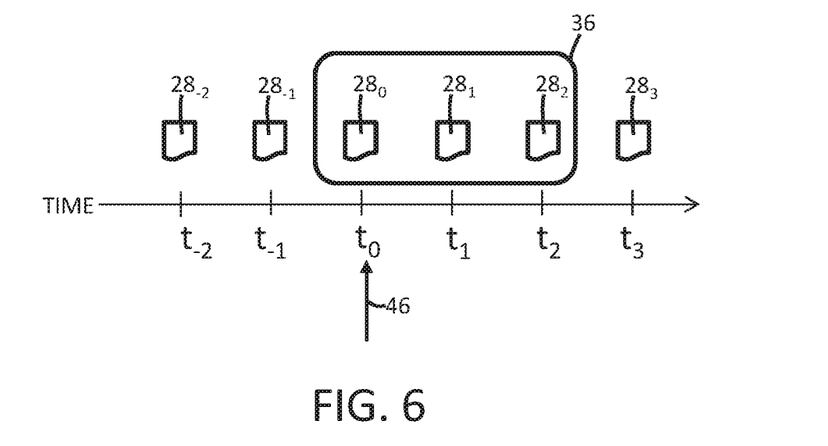
Figure 7:
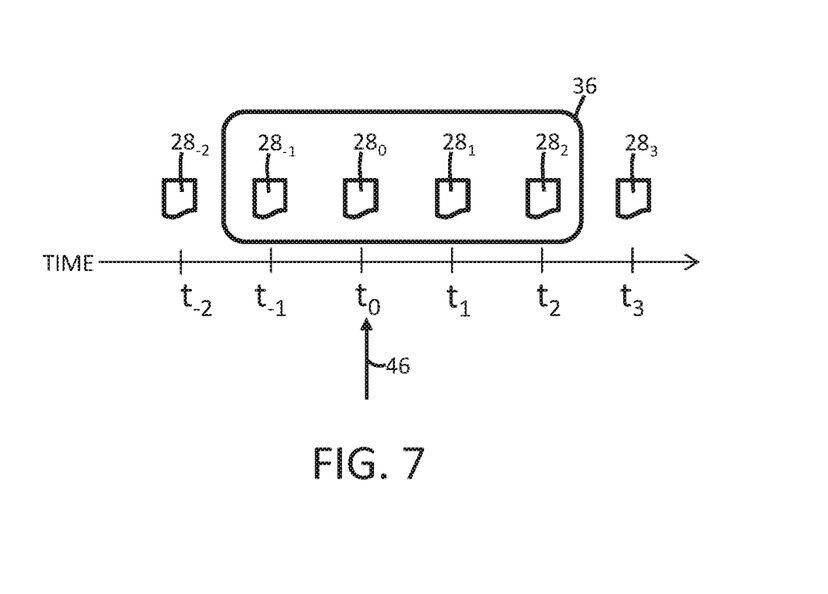

The system 10 includes a trigger 12, at least two capture devices 14, 16 (e.g., digital cameras), at least one controller 18, at least one synchronizer 20, and at least one compensator 22. The trigger 12 generates a trigger signal 24. The capture devices 14, 16 each switch from a respective idle mode to a respective recording mode upon receipt of the trigger signal 24 via a network 26. The capture devices 14, 16 each generate data packets 28, 30 when operated in the respective idle mode and the respective recording mode. The data packets 28, 30 each include sensor data indicative of a condition sensed by a sensor of the respective capture device 14, 16. The controller 18 saves data packets 28, 30 generated during the respective idle modes to a short-term memory 32, and save data packets 28, 30 generated during the respective recording modes to a long-term memory 34. The data packets 28, 30 are saved to the long-term memory 34 such that the data packets 28, 30 form respective saved data streams 36, 38 that can be retrieved and played back at a later time. The synchronizer 20 sends a sync signal 40 to the capture devices 14, 16 via the network 26. Referring to FIGS. 1 and 2, the compensator 22 determines respective delay periods 42, 44 between sending of the sync signal 40 by the synchronizer 20 (see arrow 46) and receipt of the sync signal 40 by each of the capture devices 14, 16 (see arrows 48, 50). The compensator 22 transfers from the short-term memory 32 to the long-term memory 34 any data packets 28, 30 generated during the respective delay periods 42, 44. In the illustrated embodiments, the system 10 additionally includes a display 52 configured to retrieve recorded data streams 36, 38 from the long-term memory 34 and playback the same for a user.

The trigger 12 receives a user input and generates the trigger signal 24 in response thereto. The trigger 12 can include a button, switch, or any other user input device to receive the user input.

In the illustrated embodiments, each of the capture devices 14, 16 is a digital camera capable of generating still image data and/or video image data. Thus, the capture devices 14, 16 each generate data packets 28, 30 that include image sensor data indicative of a light condition sensed by an image sensor of the respective capture device 14, 16. In some embodiments, at least one of the capture devices 14, 16 generates data packets 28, 30 that include non-image sensor data. In some such embodiments, the at least one of the capture devices 14, 16 is a medical device (e.g., an insufflator, ventilator, EKG, MRI, etc.) and includes a sensor operable to generate sensor data indicative of a condition of the patient, an operating condition of the medical device (e.g., a speed of a fan included in the medical device, a temperature of the medical device, etc.), and/or an environmental condition (e.g., light, temperature, etc.).

The capture devices 14, 16 are each switchable between a power-off state and a power-on state. In the power-on state, the capture devices 14, 16 can each be operated in at least the idle mode and the recording mode. In the idle mode, the capture devices 14, 16 can continuously generate data packets 28, 30 to be stored by the controller 18 in the short-term memory 32. The data packets 28, 30 can be generated according to a predetermined capture rate, which can be period or non-periodic. In the illustrated embodiments, continuous generation of the data packets 28, 30 starts automatically when the capture devices 14, 16 begin operating in the respective idle modes. In other embodiments, the continuous generation of the data packets 28, 30 must first be initiated by a user. As will be discussed in more detail below, in some embodiments the capture devices 14, 16 can be operated at more than one recording mode.

The number of capture devices 14, 16 included in the system 10 can vary depending on the particular application. In the illustrated embodiments, the system 10 includes a first capture device 14 and a second capture device 16. In other embodiments, the system 10 can include many more than two capture devices 14, 16.

The data packets 28, 30 generated by each of the capture devices 14, 16 include sensor data, as described above, and can also include embedded timestamps, metadata, and/or other data regarding the time, place, condition, etc., at which the data packets 28, 30 were generated. In the illustrated embodiments, the data packets 28, 30 each include metadata indicating at least the time and operating mode (e.g., idle mode, recording mode, etc.) when the respective data packet 28, 30 was generated. The timestamps, metadata, and/or other data included in the data packets 28, 30 can be used by the controller 18, the compensator 22, and/or one or more other components during the saving, processing, and/or playback of recorded data streams 36, 38.

As discussed above, the controller 18 saves the data packets 28, 30 received from the capture devices 14, 16 to the short-term memory 32 and the long-term memory 34. FIG. 2 depicts data packets 28, 30 generated by the first and second capture devices 14, 16 of the system 10 of FIG. 1 after the data packets 28, 30 have been automatically saved to the short-term memory 32 or long-term memory 34 based on whether they were generated during the respect idle modes or the respective recording modes of the capture devices 14, 16. In particular, it can be seen that the data packets 28 generated by the first capture device 14 were saved to the short-term memory 32 until receipt of the sync signal 40 by the first capture device 14 at time $t_1$ (see arrow 48). Thereafter, the data packets 28 generated by the first capture device 14 were saved to the long-term memory 34, where they collectively formed a saved data stream 36 of the first capture device 14. Similarly, it can be seen that the data packets 30 generated by the second capture device 16 were saved to the short-term memory 32 until receipt of the sync signal 40 by the second capture device 16 at time $t_2$ (see arrow 50). Thereafter, the data packets 30 generated by the second capture device 16 were saved to the long-term memory 34 where they collectively formed a saved data stream 38 of the second capture device 16.

In the illustrated embodiments, the controller 18 is a single component that receives the data packets 28, 30 from the capture devices 14, 16 via the network 26. In other embodiments, the controller 18 and/or the short-term and long-term memories 32, 34 can be directly connected to the capture devices 14, 16. That is, storage of the data packets 28, 30 in one or both of the short-term and long-term memories 32, 34 can be done remotely via the network 26 (as shown in the illustrated embodiments), or it can be done locally.

The short-term and long-term memories 32, 34 can each be one of various different types of memory devices, including, for example, a static RAM, dynamic RAM, flash memory, read only memory ROM (Read Only Memory), or another type of data storage medium. In some embodiments, the short-term memory 32 provides only temporary storage and is automatically purged of data packets 28, 30 after a predetermined amount of time, whereas the long-term memory 34 provides permanent storage.

The network 26 is a computer network such as the Internet or a subset of the Internet, a wide-area-network, local-area-network, private network of computing infrastructure, or other arrangement of interconnected computing equipment at the application, platform, or infrastructure level, or other cloud computing layers of abstraction.

The synchronizer 20 sends the sync signal 40 to the capture devices 14, 16 as described above. The sync signal 40 can be similar to the data packets 28, 30 in that it can include embedded timestamps, metadata, and/or other data indicating the time at which the sync signal 40 was sent by the synchronizer 20, and/or other relevant information that can be used to perform the functionality described herein. The sync signal 40 and the information embedded therewith is used by the compensator 22 to perform the functionality described herein.

The synchronizer 20 is disposed relative to the trigger 12, the capture devices 14, 16, and the network 26 such that respective delay periods 42, 44 between sending of the sync signal 40 and receipt of the sync signal 40 by each of the capture devices 14, 16 is identical to respective delay periods between sending of the trigger signal 24 and receipt of the trigger signal 24 by each of the capture devices 14, 16.

In the illustrated embodiments, the synchronizer 20 repeatedly sends the sync signal 40 to the capture devices 14, 16 via the network 26, and the compensator 22 repeatedly determines the respective delay periods 42, 44 of the capture devices 14, 16. The cycle of sending the sync signal 40 and determining the respective delay periods 42, 44 can be repeated throughout operation of the capture devices 14, 16 in the respective idle modes and recording modes. The repetition of the cycle can be periodic or non-periodic.

In some embodiments, the synchronizer 20 repeatedly sends the sync signal 40 in order to generate a common and aligned time basis that is used by one or more other components of the system 10 (e.g., the capture devices 14, 16, the compensator 22). The time basis can be periodic or non-periodic, and need not have any relation to real time. For example, the time basis can be an arbitrary, regularly repeating signal. Additionally or alternatively, user initiated events can be used to form the time basis. In some embodiments, the predetermined capture rate at which the data packets 28, 30 are generated is an integer multiple or divisor of a period rate at which the sync signal 40 is sent to the capture devices 14, 16.

Figure 8:
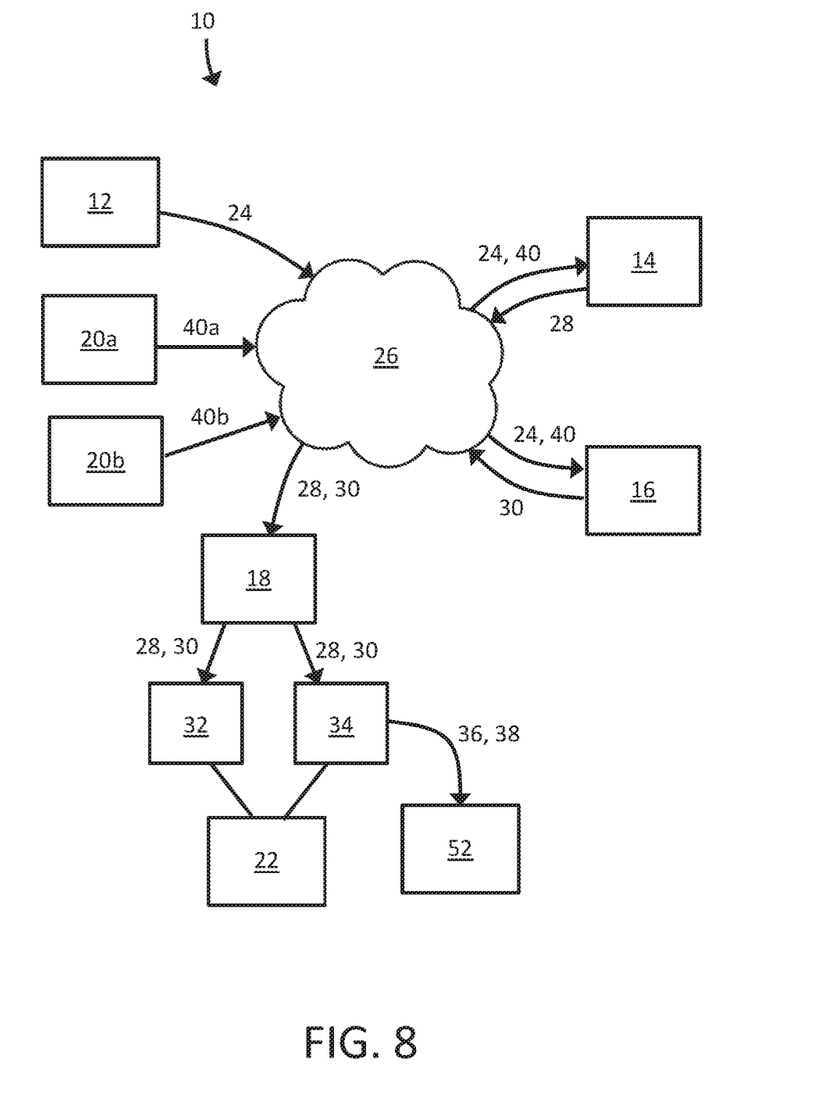
FIG. 8 schematically illustrates another embodiment of the present system.
Figure 9:
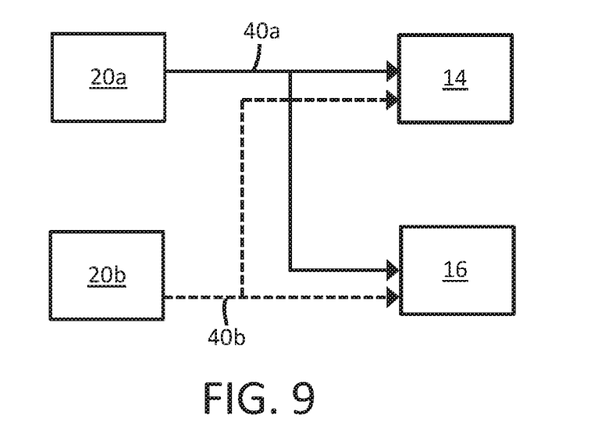
FIG. 9 schematically illustrates a connection between the synchronizer and the capture devices of the system of FIG. 8.
Figure 10:
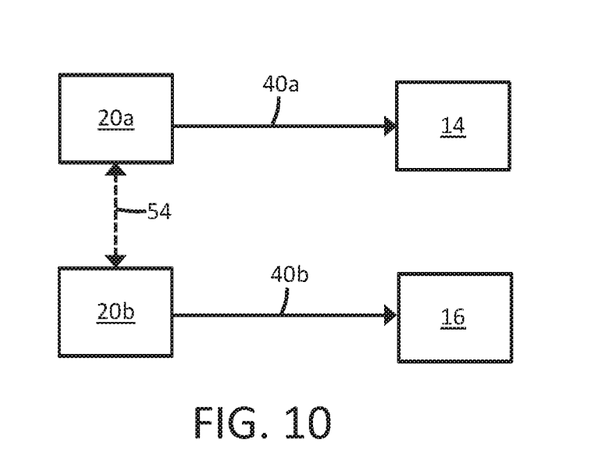
FIG. 10 schematically illustrates an alternative connection between the synchronizer and the capture devices of the system of FIG. 8.

In the embodiment illustrated in FIG. 1, the system 10 includes a single synchronizer 20 that sends the same sync signal 40 to each of the capture devices 14, 16. In other embodiments, the system 10 includes more than one synchronizer 20. In the embodiment illustrated in FIG. 8, for example, the system 10 includes a first synchronizer 20a and a second synchronizer 20b. Referring to FIG. 9, in some such embodiments, the first synchronizer 20a can be a primary unit that sends a sync signal 40a to both of the capture devices 14, 16, and the second synchronizer 20b can be a secondary unit that sends a sync signal 40b to both of the capture devices 14, 16 only when first synchronizer 20a is unavailable (e.g., due to error, absence, power-off status, etc.). Referring to FIG. 10, in other embodiments, the first and second synchronizers 20a, 20b can be configured such that the first synchronizer 20a sends a sync signal 40a to the first capture device 14 and, in parallel, the second synchronizer 20b sends a sync signal 40b to the second capture device 16. In such embodiments, the first and second synchronizers 20a, 20b can be synchronized with one another via a connection 54 therebetween.

The compensator 22 is in communication with the short-term and long-term memories 32, 34. In the illustrated embodiments, the connection therebetween is direct. In other embodiments, the compensator 22 can be connected to the short-term and/or long-term memories 32, 34 via the network 26. The compensator 22 is also in direct and/or indirect communication with the synchronizer 20, which allows the compensator 22 to determine the time between sending of the sync signal 40 by the synchronizer 20 (see arrow 46) and receipt of the sync signal 40 by each of the capture devices 14, 16 (see arrows 48, 50), as discussed above.

As described above, the compensator 22 determines respective delay periods 42, 44 and transfers from the short-term memory 32 to the long-term memory 34 any data packets 28, 30 generated during the respective delay periods 42, 44. Referring again to FIG. 2, it can be seen that the delay period 42 for the first capture device 14 is determined by the compensator 22 to be the difference between the time $t_0$ when the trigger signal 24 was sent by the trigger 12 (hereinafter the "trigger time $t_0$") and the time $t_1$ when the sync signal 40 was received by the first capture device 14 (see arrow 48). Similarly, the delay period 44 for the second capture device 16 is calculated to be the difference between the trigger time $t_0$ and the time $t_2$ when the sync signal 40 was received by the second capture device 16 (see arrow 50). The data packets $28_0$, $30_0$, and $30_1$ are shown to be the ones that will be transferred from the short-term memory 32 to the long-term memory 34 by the compensator 22, because they were generated during the respective delay periods 42, 44.

In some embodiments, the compensator 22 also removes data packets 28, 30 from ends of the saved data streams 36, 38 to provide saved data streams 36, 38 with predetermined numbers of data packets 36, 38. Additionally or alternatively, the compensator 22 can transfer data packets 36, 38 from the short-term memory 32 to the saved data streams 36, 38 to provide the saved data streams 36, 38 with a predetermined number of data packets 36, 38. The predetermined number of data packets 36, 38 in the resulting saved data streams 36, 68 can vary depending on the type of recording mode in which the capture devices 36, 38 are being operated.

FIGS. 3-7 illustrate several different recording modes. In each of the recording modes shown in FIGS. 3-7, the saved data stream 36 includes at least the data packet 28 generated at the trigger time $t_0$. In the recording mode shown in FIG. 4, the saved data stream 36 additionally includes a single data packet 28 generated before the trigger time $t_0$ (i.e., data packet $28_{-1}$) and a single data packet 28 generated after the trigger time $t_0$ (i.e., data packet $28_1$). In the recording mode shown in FIG. 5, the saved data stream 36 additionally includes more than one data packet 28 generated before the trigger time $t_0$ (e.g., data packets $28_{-1}$ and $28_{-2}$). In the recording mode shown in FIG. 6, the saved data stream 36 additionally includes more than one data packet 28 generated after the trigger time $t_0$ (e.g., data packets $28_1$ and $28_2$). In the recording mode shown in FIG. 7, the saved data stream 36 additionally includes more than one data packet 28 generated before the trigger time $t_0$ (e.g., data packets $28_{-1}$ and $28_{-2}$) and more than one data packet 28 generated after the trigger time $t_0$ (e.g., data packets $28_1$ and $28_2$).

The above-described functionalities of the system 10 overcome the above-described problems with known synchronization techniques. Among other things, the system 10 provides multiple network-connected capture devices 14, 16 configured to generate recorded data streams 36, 38 that start at least as early as the time $t_0$ that the trigger signal 24 is sent by the trigger 12 via the network 26. The system 10 enables perfectly synchronized viewing and/or playback of the recorded data streams 36, 38, and permits time-accurate switching between recorded data streams 36, 38 during playback (e.g., via display 52). The system 10 is able to account for the fact that delay times 42, 44 between the trigger 12 and each of the capture devices 14, 16 can change relative to one another over time due to changing conditions of the network 26. The system 10 also permits synchronization and correlation of image data with other non-image data captured during recording.

The respective functionalities of the various components and sub-components of the system 10 can be implemented in various different ways, including use of analog and/or digital hardware (e.g., counters, switches, logic devices, memory devices, programmable processors, non-transitory computer-readable storage mediums), software, firmware, or combinations thereof. The various components and sub-components of the system 10 can be specially constructed to perform the desired functionality, and/or can include one or more general purpose computers selectively configured to perform the desired functionality. In some embodiments, the system 10 and/or the various components and subcomponents thereof can perform one or more of the functions described herein by executing software, which can be stored, for example, on a non-transitory computer-readable storage medium. In view of the present disclosure, a person having ordinary skill in the art would be able to assemble and/or adapt (e.g., construct, program) the various components and sub-components of the system 10 to perform the functionality described herein without undue experimentation.

Although some components of the system 10 are described herein as being discrete components separate from one another, in some embodiments one or more of those components can be combined into a single component. For example, although the trigger 12 and the synchronizer 20 are described herein as being discrete components separate from one another, in some embodiments one or more of those components can be combined into a single component.

Referring to FIG. 1, another aspect of the present invention involves a method that includes the steps of: (i) connecting the trigger 12 and the synchronizer 20 to the capture devices 14, 16 via the network 26; (ii) sending the trigger signal 24 generated by the trigger 12 to the capture devices 14, 16 via the network 26 to thereby cause each of the capture devices 14, 16 to switch from the respective idle mode to the respective recording mode; (iii) saving data packets 28, 30 generated during the respective idle modes to a short-term memory 32, and saving data packets 28, 30 generated during the recording mode to a long-term memory such that the data packets form respective saved data streams 36, 38; (iv) sending a sync signal to the at least two capture devices via the network; (v) determining respective delay periods between sending of the sync signal by the synchronizer and receipt of the sync signal by each of the at least two capture devices; and (vi) transferring from the short-term memory to the long-term memory any data packets generated during the respective delay periods.

As will be apparent in view of the above-described functionality of the system 10 and the various components thereof, the steps of the method can include various sub-steps, and/or various other steps in addition to the above-described steps. Although the steps of the method are set forth in a particular order using alphanumeric labels, the labels are used merely for convenient identification of steps, and are not intended to imply, specify, or require a particular order of carrying out such steps. Furthermore, in some embodiments, the method can include more or less steps than those discussed herein.

The terms "determining," "generating," and "recording," "sending," "saving," etc., and variations thereof, are each used herein to refer to one or more actions and/or processes that can be implemented, for example, at least in part via a programmable processor or similar electronic computing device by manipulating and/or transforming data within processor memory into other data within processor memory.

The present disclosure describes aspects of the present invention with reference to the exemplary embodiments illustrated in the drawings; however, aspects of the present invention are not limited to the exemplary embodiments illustrated in the drawings. It will be apparent to those of ordinary skill in the art that aspects of the present invention include many more embodiments. Accordingly, aspects of the present invention are not to be restricted in light of the exemplary embodiments illustrated in the drawings. It will also be apparent to those of ordinary skill in the art that variations and modifications can be made without departing from the true scope of the present disclosure. For example, in some instances, one or more features disclosed in connection with one embodiment can be used alone or in combination with one or more features of one or more other embodiments.

What is claimed is:

1. A system, comprising:
    a trigger configured to generate a trigger signal;
    at least two capture devices, each configured to switch from a respective idle mode to a respective recording mode upon receipt of the trigger signal via a network, and each configured to generate data packets when operated in the respective idle mode and the respective recording mode, the data packets each including sensor data indicative of a condition sensed by a sensor of the respective capture device;
    a controller configured to save data packets generated during the respective idle modes to a short-term memory, and configured to save data packets generated during the respective recording modes to a long-term memory such that the data packets form respective saved data streams, each of the saved data streams including a first-generated data packet at a beginning thereof and a last-generated data packet at an end thereof;
    a synchronizer configured to send a sync signal to the at least two capture devices via the network; and
    a compensator configured to: (i) determine respective delay periods between sending of the sync signal by the synchronizer and receipt of the sync signal by each of the at least two capture devices; (ii) transfer from the short-term memory to the long-term memory any data packets generated during the respective delay periods; and (iii) remove at least one data packet from the end of at least one of the saved data streams.

2. The system of claim 1, wherein the trigger is configured to receive a user input and generate the trigger signal in response thereto.

3. The system of claim 1, wherein at least one of the at least two capture devices is a camera.

4. The system of claim 3, wherein the camera is at least one of a still image camera and a video image camera.

5. The system of claim 1, wherein the at least two capture devices are each configured to generate data packets that include video image data.

6. The system of claim 1, wherein at least one of the at least two capture devices is configured to generate data packets that include non-image sensor data.

7. The system of claim 6, wherein the at least one of the at least two capture devices that is configured to generate data packets that include non-image sensor data is a medical device, wherein the medical device includes a sensor operable to generate sensor data indicative of a condition of a patient condition, an operating condition of the medical device, and/or an environmental condition.

8. The system of claim 1, wherein the at least two capture devices, when operated in the respective idle modes, continuously generate data packets.

9. The system of claim 1, wherein the at least two capture devices, when operated in the respective idle modes, continuously generate data packets according to a predetermined capture rate.

10. The system of claim 9, wherein the predetermined capture rate is an integer multiple or divisor of a period rate at which the sync signal is repetitively sent to the at least two capture devices.

11. The system of claim 1, wherein the data packets generated by the at least two capture devices further include metadata.

12. The system of claim 1, wherein the network is at least one the Internet, a wide-area-network, local-area-network, and a private network of computing infrastructure.

13. The system of claim 1, wherein the synchronizer has a time basis that is the same as, and aligned with, respective time bases of the at least two capture devices.

14. The system of claim 1, wherein the synchronizer is disposed relative to the trigger and the network such that respective delay periods between sending of the sync signal and receipt of the sync signal by each of the at least two capture devices is identical to respective delay periods between sending of the trigger signal and receipt of the trigger signal by each of the at least two capture devices.

15. The system of claim 1, wherein the synchronizer is configured to repeatedly send the sync signal to the at least two capture devices via the network, and the compensator is configured to repeatedly determine the respective delay periods of the at least two capture devices.

16. The system of claim 15, wherein the synchronizer is configured to repeatedly send the sync signal and the compensator is configured to repeatedly determine the respective delay periods according to a repetitive cycle.

17. The system of claim 1, wherein the synchronizer includes a first synchronizer and a second synchronizer, the first synchronizer configured to send the sync signal to the at least two capture devices, and the second synchronizer configured to send the sync signal to the at least two capture devices when the first synchronization is unavailable to do so.

18. The system of claim 1, wherein the synchronizer includes a first synchronizer and a second synchronizer, the first synchronizer configured to send the sync signal to a first capture device of the at least two capture devices, and the second synchronizer configured to send the sync signal to a second capture device of the at least two capture devices.

19. The system of claim 18, wherein the first synchronizer and the second synchronizer are synchronized with one another via a connection therebetween.

20. The system of claim 1, wherein the compensator is further configured to transfer from the short-term memory to the long-term memory a predetermined number of data packets generated before generation of the trigger signal by the trigger.

21. The system of claim 1, further comprising a display configured to retrieve saved data streams from the long-term memory and replay the saved data streams for a user.

22. A method, comprising:
connecting a trigger and a synchronizer to at least two capture devices via a network, the at least two capture devices each configured to generate data packets when operated in a respective idle mode and a respective recording mode, the data packets each including sensor data indicative of a condition sensed by a sensor of the respective capture device;
sending a trigger signal generated by the trigger to the at least two capture devices via the network to thereby cause each of the at least two capture devices to switch from the respective idle mode to the respective recording mode;
saving data packets generated during the respective idle modes to a short-term memory, and saving data packets generated during the recording mode to a long-term memory such that the data packets form respective saved data streams, each of the saved data streams including a first-generated data packet at a beginning thereof and a last-generated data packet at an end thereof;
sending a sync signal to the at least two capture devices via the network;
determining respective delay periods between sending of the sync signal by the synchronizer and receipt of the sync signal by each of the at least two capture devices;
transferring from the short-term memory to the long-term memory any data packets generated during the respective delay periods; and
removing at least one data packet from the end of at least one of the saved data streams.

23. A system, comprising:
a trigger configured to generate a trigger signal;
at least two capture devices, each configured to switch from a respective idle mode to a respective recording mode upon receipt of the trigger signal via a network, and each configured to generate data packets when operated in the respective idle mode and the respective recording mode, the data packets each including sensor data indicative of a condition sensed by a sensor of the respective capture device;
a controller configured to save data packets generated during the respective idle modes to a short-term memory, and configured to save data packets generated during the respective recording modes to a long-term memory such that the data packets form respective saved data streams, each of the saved data streams including an oldest data packet at a beginning thereof and a newest data packet at an end thereof;
a synchronizer configured to send a sync signal to the at least two capture devices via the network; and
a compensator configured to: (i) determine respective delay periods between sending of the sync signal by the synchronizer and receipt of the sync signal by each of the at least two capture devices; (ii) transfer from the short-term memory to the long-term memory any data packets generated during the respective delay periods; and (iii) remove at least one data packet from the end of at least one of the saved data streams.

* * * * *